United States Patent
Nakashima et al.

(10) Patent No.: US 11,685,753 B2
(45) Date of Patent: Jun. 27, 2023

(54) METAL ALKOXIDE, AND AQUEOUS RESIN CROSSLINKING COMPOSITION AND AQUEOUS RESIN COMPOSITION WHICH USE SAME

(71) Applicant: NISSHINBO CHEMICAL INC., Tokyo (JP)

(72) Inventors: Shinichi Nakashima, Chiba (JP); Kenichi Yanagisawa, Chiba (JP)

(73) Assignee: NISSHINBO CHEMICAL INC., Tokyo (JP)

( * ) Notice: Subject to any disclaimer, the term of this patent is extended or adjusted under 35 U.S.C. 154(b) by 533 days.

(21) Appl. No.: 16/970,902

(22) PCT Filed: Jan. 18, 2019

(86) PCT No.: PCT/JP2019/001371
§ 371 (c)(1),
(2) Date: Aug. 18, 2020

(87) PCT Pub. No.: WO2019/163344
PCT Pub. Date: Aug. 29, 2019

(65) Prior Publication Data
US 2020/0385413 A1    Dec. 10, 2020

(30) Foreign Application Priority Data
Feb. 23, 2018   (JP) .................................. 2018-031214

(51) Int. Cl.
| | | |
|---|---|---|
| C07F 7/28 | (2006.01) | |
| C07F 5/06 | (2006.01) | |
| C07F 7/00 | (2006.01) | |
| C08K 5/057 | (2006.01) | |
| C08K 5/06 | (2006.01) | |
| C08K 5/29 | (2006.01) | |
| C08K 5/353 | (2006.01) | |
| C08L 33/08 | (2006.01) | |
| C08L 75/04 | (2006.01) | |

(52) U.S. Cl.
CPC ................ *C07F 7/28* (2013.01); *C07F 5/069* (2013.01); *C07F 7/003* (2013.01); *C08K 5/057* (2013.01); *C08K 5/06* (2013.01); *C08K 5/29* (2013.01); *C08K 5/353* (2013.01); *C08L 33/08* (2013.01); *C08L 75/04* (2013.01)

(58) Field of Classification Search
CPC ......... C08L 79/00; C08L 79/02; C08K 5/057; C08K 5/29; C08K 5/353
See application file for complete search history.

(56) References Cited

U.S. PATENT DOCUMENTS

| | | |
|---|---|---|
| 3,817,889 A | 6/1974 | Fink et al. |
| 4,775,653 A | 10/1988 | Leach et al. |
| 5,821,325 A | 10/1998 | Yahata et al. |
| 6,124,398 A * | 9/2000 | Imashiro .............. C08G 18/283 525/61 |
| 2012/0034315 A1 * | 2/2012 | Hanagan ................ A01N 43/84 514/266.3 |
| 2018/0371237 A1 | 12/2018 | Tsukamoto et al. |
| 2021/0032454 A1 * | 2/2021 | Nakashima .......... C08G 18/283 |

FOREIGN PATENT DOCUMENTS

| | | | |
|---|---|---|---|
| GB | 941692 A | 11/1963 | |
| JP | 47-20206 B1 | 6/1972 | |
| JP | 6-86936 A | 3/1994 | |
| JP | 9-216931 A | 8/1997 | |
| JP | 9-221532 A | 8/1997 | |
| JP | 2904-217767 A | 8/2004 | |
| JP | 2004-256505 A | 9/2004 | |
| JP | 2007-297491 A | 11/2007 | |
| JP | 2009-132762 A | 6/2009 | |
| JP | 2014-140797 A | 8/2014 | |
| JP | 2017-114857 A | 6/2017 | |
| WO | WO-2016133056 A1 * | 8/2016 | ............. C08K 5/098 |
| WO | WO 2017/006950 A1 | 1/2017 | |

OTHER PUBLICATIONS

Extended European Search Report for European Application No. 19757887.9, dated Oct. 20, 2021.
Japanese Office Action for Japanese Application No. 2018-031214, dated Sep. 7, 2021.
Ochi et al., "Synthesis and Properties of Surface Active Organotitanium Compounds", Bulletin of the Chemical Society of Japan, vol. 40, No. 4, Apr. 1967, pp. 983-987.
International Search Report for PCT/JP2019/001371 (PCT/ISA/210) dated Mar. 5, 2019.

* cited by examiner

*Primary Examiner* — Michael M Dollinger
(74) *Attorney, Agent, or Firm* — Birch, Stewart, Kolasch & Birch, LLP

(57) ABSTRACT

The present invention provides a novel metal alkoxide having excellent hydrolysis resistance, and a crosslinking agent composition for aqueous resin and an aqueous resin composition each using the same. A metal alkoxide represented by the following formula (1-1), (1-2), or (1-3) and having a mass average molecular weight of 800 to 8,500 is used:

$$Ti(OA)_4 \quad (1\text{-}1)$$

$$Zr(OA)_4 \quad (1\text{-}2)$$

$$Al(OA)_3 \quad (1\text{-}3)$$

wherein A's are each independently a residue resulting from removal of a hydroxy group from a polyalkylene glycol monohydrocarbyl ether represented by the following general formula (1a):

$$R^{11}(OCHR^{12}CH_2)_nOH \quad (1a)$$

wherein $R^{11}$ is an alkyl group having 1 to 4 carbon atoms or a phenyl group; $R^{12}$ is a hydrogen atom or an alkyl group having 1 to 4 carbon atoms; and n is an integer of 4 to 45.

2 Claims, No Drawings

METAL ALKOXIDE, AND AQUEOUS RESIN CROSSLINKING COMPOSITION AND AQUEOUS RESIN COMPOSITION WHICH USE SAME

TECHNICAL FIELD

The present invention relates to a novel metal alkoxide, and a crosslinking agent composition for aqueous resin and an aqueous resin composition each using the same.

BACKGROUND ART

An aqueous resin having water solubility or water dispersibility is used for various applications, such as paints, inks, fiber processing agents, adhesives, and coating agents, because of excellent handling properties from the standpoint of environment and safety. As for the aqueous resin, in order to give water solubility or water dispersibility to the resin itself, a hydrophilic group, such as a hydroxy group and a carboxy group, is introduced. Therefore, the aqueous resin is liable to be inferior in water resistance or durability to an oily resin.

For that reason, in order to improve various physical properties of an aqueous resin, such as water resistance, durability, and strength, a crosslinking agent is added in the foregoing aqueous resin.

As such a crosslinking agent, a polycarbodiimide and a polyoxazoline are known. For example, PTLs 1 and 2 describe that by allowing a polycarbodiimide to react with a compound having a hydroxy group or a mercapto group in the presence of an alcoholate (alkoxide) of an alkali metal or alkaline earth metal, a crosslinking reaction by a carbodiimide group is promoted.

In addition, PTLs 3 and 4 propose, as a crosslinking agent that is hardly hydrolyzed, an aqueous titanium composition composed of a titanium alkoxide or a titanium chelate compound, an amine compound, and a glycol compound.

CITATION LIST

Patent Literature

PTL 1: JP 9-221532 A
PTL 2: JP 9-216931 A
PTL 3: JP 2004-256505 A
PTL 4: JP 2009-132762 A

SUMMARY OF INVENTION

Technical Problem

However, in the aforementioned PTLs 1 and 2, the alkali metal or alkaline earth metal is used as the metal of the metal alkoxide, such is easily hydrolyzed, and the reaction system becomes strongly alkaline, so that it is not preferred from the standpoint of safety at the time of handling. For this reason, it may not be said that crosslinking by the methods described in PTLs 1 and 2 is adaptive to the aqueous resin.

Meanwhile, the aqueous titanium compositions described in the aforementioned PTLs 3 and 4 contain the amine compound as an essential component but are not one containing, as the component, a polycarbodiimide or a polyoxazoline. When a carbodiimide group-containing component is mixed with the foregoing aqueous titanium composition, an amine and a carbodiimide group readily react with each other, whereby a crosslinking-reactive functional group (crosslinking group) is decreased. In the case of an oxazoline group-containing component, the same phenomenon is caused.

In addition, the polycarbodiimide and the polyoxazoline are in general low in reactivity relative to an alcoholic hydroxy group, so that there was involved such a problem that the crosslinking reaction does not thoroughly proceed relative to an aqueous resin having a high content proportion of the alcoholic hydroxy group.

Under these circumstances, in order to improve the crosslinking reactivity of the polycarbodiimide relative to the crosslinking group of the alcoholic hydroxy group, the present inventors made extensive and intensive investigations. As a result, they have found a novel metal alkoxide which is excellent in hydrolysis resistance and is able to produce an aqueous resin cured product having a high crosslinking degree through joint use with the polycarbodiimide. In addition, the present inventors have also obtained such a finding that the metal alkoxide brings about the same effects relative to the polyoxazoline.

Furthermore, the present inventors have also obtained such a finding that the metal alkoxide improves crosslinking reactivity relative to a crosslinking group of a carboxy group with respect to all of the polycarbodiimide and the polyoxazoline.

The present invention has been made on the basis of these findings, and an object thereof is to provide a novel metal alkoxide having excellent hydrolysis resistance, and a crosslinking agent composition for aqueous resin and an aqueous resin composition each using the same.

Solution to Problem

The present invention is based on such a finding that an alkoxide of titanium, zirconium, or aluminum having a substituent derived from a polyalkylene glycol monohydrocarbyl ether has excellent hydrolysis resistance.

Specifically, the present invention provides the following [1] to [4].

[1] A metal alkoxide represented by the following formula (1-1), (1-2), or (1-3) and having a mass average molecular weight of 800 to 8,500:

$$Ti(OA)_4 \quad (1\text{-}1)$$

$$Zr(OA)_4 \quad (1\text{-}2)$$

$$Al(OA)_3 \quad (1\text{-}3)$$

wherein A's are each independently a residue resulting from removal of a hydroxy group from a polyalkylene glycol monohydrocarbyl ether represented by the following general formula (1a):

$$R^{11}(OCHR^{12}CH_2)_nOH \quad (1a)$$

wherein $R^{11}$ is an alkyl group having 1 to 4 carbon atoms or a phenyl group; $R^{12}$ is a hydrogen atom or an alkyl group having 1 to 4 carbon atoms; and n is an integer of 4 to 45.

[2] A metal alkoxide represented by the following formula (2-1), (2-2), or (2-3) and having a mass average molecular weight of 600 to 6,000:

$$Ti(OA)_p(OR)_{4-p} \quad (2\text{-}1)$$

$$Zr(OA)_q(OR)_{4-q} \quad (2\text{-}2)$$

$$Al(OA)_r(OR)_{3-r} \quad (2\text{-}3)$$

wherein A's are each independently a residue resulting from removal of a hydroxy group from a polyalkylene glycol monohydrocarbyl ether represented by the following general formula (1a); R's are each independently an alkyl group having 1 to 20 carbon atoms; p and q are each a number of 2 or more and less than 4; and r is a number of 2 or more and less than 3:

$$R^{11}(OCHR^{12}CH_2)_nOH \quad (1a)$$

wherein $R^{11}$ is an alkyl group having 1 to 4 carbon atoms or a phenyl group; $R^{12}$ is a hydrogen atom or an alkyl group having 1 to 4 carbon atoms; and n is an integer of 4 to 45.

[3] A crosslinking agent composition for aqueous resin, containing the metal alkoxide as set forth in the above [1] or [2] and at least one compound selected from a polycarbodiimide and a polyoxazoline.

[4] An aqueous resin composition containing at least one aqueous resin containing at least any one of an alcoholic hydroxy group and a carboxy group, at least one compound selected from a polycarbodiimide and a polyoxazoline, and the metal alkoxide as set forth in the above [1] or [2].

Advantageous Effects of Invention

In accordance with the present invention, a novel metal alkoxide that is an alkoxide of titanium, zirconium, or aluminum is provided. The aforementioned metal alkoxide has excellent hydrolysis resistance and is able to improve crosslinking reactivity of a polycarbodiimide and/or a polyoxazoline relative to a hydrophilic crosslinking group.

For this reason, the metal alkoxide of the present invention constitutes an excellent crosslinking agent composition for aqueous resin together with the polycarbodiimide and/or the polyoxazoline and further, is able to provide an aqueous resin composition which is excellent in crosslinking reactivity.

Description of Embodiments

The metal alkoxide of the present invention, and the crosslinking agent composition for aqueous resin and the aqueous resin composition each using the same are hereunder described in detail.

The term "aqueous" as referred to in the present invention means that solubility or dispersibility relative to an aqueous solvent is revealed. The aqueous solvent refers to water or a hydrophilic solvent selected from an alcohol, an ether, a ketone, an ester, and so on, or a mixed solvent thereof.

[Metal Alkoxide]

As the metal alkoxide of the present invention, there are provided a metal alkoxide (X) according to a first embodiment and a metal alkoxide (Y) according to a second embodiment as mentioned below.

(Metal Alkoxide (X))

The metal alkoxide (X) according to a first embodiment of the present invention is represented by the following formula (1-1), (1-2), or (1-3) and has a mass average molecular weight of 800 to 8,500. The metal alkoxide (X) is a novel metal alkoxide and is excellent in hydrolysis resistance.

$$Ti(OA)_4 \quad (1-1)$$

$$Zr(OA)_4 \quad (1-2)$$

$$Al(OA)_3 \quad (1-3)$$

In the formulae (1-1) to (1-3), A's are each independently a residue resulting from removal of a hydroxy group from a polyalkylene glycol monohydrocarbyl ether represented by the following general formula (1a);

$$R^{11}(OCHR^{12}CH_2)_nOH \quad (1a)$$

In the formula (1a), $R^{11}$ is an alkyl group having 1 to 4 carbon atoms or a phenyl group, preferably a methyl group or an ethyl group, and more preferably a methyl group; $R^{12}$ is a hydrogen atom or an alkyl group having 1 to 4 carbon atoms, preferably a hydrogen atom or a methyl group, and more preferably a hydrogen atom; and n is an integer of 4 to 45, preferably 5 to 30, and more preferably 6 to 15.

From the viewpoint of handling properties and easiness of availability, and so on, the polyalkylene glycol monohydrocarbyl ether is preferably a polyalkylene glycol monoalkyl ether. Specifically, examples thereof include polyethylene glycol monomethyl ether and polyethylene glycol monoethyl ether, with polyethylene glycol monomethyl ether being especially preferred.

The metal alkoxide (X) has a mass average molecular weight of 800 to 8,500, preferably 800 to 8,000, and more preferably 1,000 to 8,000.

It may be considered that the hydrolysis of a metal alkoxide proceeds due to the fact that the constituent metal atom and the water molecule approach to each other. The constituent metal atom (central metal atom) of the metal alkoxide (X) is hindered from approach to the water molecule due to steric hindrance of the metal alkoxide (X). When the mass average molecular weight of the metal alkoxide (X) is less than 800, a steric hindrance effect is small, and the hydrolysis proceeds, so that a catalytic function to improve the crosslinking reactivity as mentioned later is not sufficiently obtained. On the other hand, in the case where the foregoing mass average molecular weight is more than 8,500, the formula weight of the metal alkoxide (X) is large, and the concentration of the central metal atom in the molecule becomes relatively low, so that the catalytic function is not sufficiently obtained.

The mass average molecular weight of the metal alkoxide (X) in the present invention is a calculated value determined from a molecular weight of the raw material or the like. This mass average molecular weight can also be measured by means of gel permeation chromatography (GPC).

The constituent metal atom of the metal alkoxide (X) is a titanium atom, a zirconium atom, or an alumina atom. The metal alkoxide of an alkali metal or alkaline earth metal is very ease to be hydrolyzed, whereas the metal alkoxide (X) in which the metal atom is titanium, zirconium, or aluminum is excellent in hydrolysis resistance.

Although a production method of the metal alkoxide (X) is not particularly limited, for example, the metal alkoxide (X) can be obtained by using, as a raw material, a commercially available titanium tetraalkoxide, zirconium tetraalkoxide, or aluminum trialkoxide, each of which is a metal alkoxide of a lower alcohol having 1 to 4 carbon atoms, and subjecting all of the respective alkoxy groups thereof to a substitution reaction with a predetermined polyalkylene glycol monohydrocarbyl ether by a known method.

(Metal Alkoxide (Y))

The metal alkoxide (Y) according to a second embodiment of the present invention is a compound represented by the following formula (2-1), (2-2), or (2-3) and having a mass average molecular weight of 600 to 6,000.

$$Ti(OA)_p(OR)_{4-p} \quad (2-1)$$

$$Zr(OA)_q(OR)_{4-q} \quad (2-2)$$

$$Al(OA)_r(OR)_{3-r} \quad (2-3)$$

Similar to the metal alkoxide (X), the constituent metal atom of the metal alkoxide (Y) is a titanium atom, a zirconium atom, or an aluminum atom.

In the formulae (2-1) to (2-3), A is the same as A in the metal alkoxide (X).

R's are each independently an alkyl group having 1 to 20 carbon atoms. From the viewpoint of handling properties and easiness of availability of the raw material, and so on, examples of the alkyl group include a methyl group, an ethyl group, a n-propyl group, an isopropyl group, a n-butyl group, a tertiary butyl group, an octyl group, and a stearyl group.

p and q are each a number of 2 or more and less than 4; and r is a number of 2 or more and less than 3. In the metal alkoxides represented by the formulae (2-1) to (2-3), in order that the constituent metal atom (central metal atom) of the metal alkoxide (X) may be hindered from approach to the water molecule, p, q, and r are each set to 2 or more. In addition, these metal alkoxides each have an alkoxy group (OR), and p and q are each set to less than 4, and r is set to less than 3.

p represents an average value of the number of the alkoxy group (OA) bonding to the titanium atom in one molecule of the titanium alkoxide represented by the formula (2-1) and is a number of 2 or more and less than 4, and it is not limited to an integer. In the titanium alkoxide represented by the formula (2-1), the alkoxy group (OA) and the alkoxy group (OR) are bonded in a total number of 4 to the titanium atom. This titanium alkoxide may be one kind of alkoxide in which the alkoxy group (OA) is bonded in a number of 2 or 3, or may be a mixture of alkoxides in which the alkoxy group is bonded in an integer number of 0 to 4.

In the case of the mixture, the average number of the alkoxy group (OA) per molecule is expressed in terms of p.

Similarly, q also represents an average value of the number of alkoxy groups (OA) bonding to the zirconium atom in one molecule of the zirconium alkoxide represented by the formula (2-2) and is a number of 2 or more and less than 4, and it is not limited to an integer. That is, in the zirconium alkoxide represented by the formula (2-2), the alkoxy group (OA) and the alkoxy group (OR) are bonded in a total number of 4 to the zirconium atom. This zirconium alkoxide may be one kind of alkoxide in which the alkoxy group (OA) is bonded in a number of 2 or 3, or may be a mixture of alkoxides in which the alkoxy group is bonded in an integer number of 0 to 4.

In the case of the mixture, the average number of the alkoxy group (OA) per molecule is expressed in terms of q.

r also represents an average value of the number of alkoxy groups (OA) bonding to the aluminum atom in one molecule of the aluminum alkoxide represented by the formula (2-3) and is a number of 2 or more and less than 3, and it is not limited to an integer. That is, in the aluminum alkoxide represented by the formula (2-3), the alkoxy group (OA) and the alkoxy group (OR) are bonded in a total number of 3 to the aluminum atom. This aluminum alkoxide may be one kind of alkoxide in which the alkoxy group (OA) is bonded in a number of 2, or may be a mixture of alkoxides in which the alkoxy group is bonded in an integer number of 0 to 3.

In the case of the mixture, the average number of the alkoxy group (OA) per molecule is expressed in terms of r.

A mass average molecular weight of the metal alkoxide (Y) is 600 to 6,000, preferably 700 to 5,000, and more preferably 800 to 4,000 from the viewpoint of hydrophilicity and catalytic function of the foregoing metal alkoxide.

The mass average molecular weight of the metal alkoxide (Y) can be determined in the same manner as in the mass average molecular weight of the metal alkoxide (X).

A production method of the metal alkoxide (Y) is not particularly limited, and for example, similar to the production method of the metal alkoxide (X), the metal alkoxide (Y) can be obtained by using, as a raw material, a commercially available titanium tetraalkoxide, zirconium tetraalkoxide, or aluminum trialkoxide, each of which is a metal alkoxide of a lower alcohol having 1 to 4 carbon atoms, subjecting the respective alkoxy groups thereof to a substitution reaction with a predetermined polyalkylene glycol monohydrocarbyl ether, and controlling a substitution degree of the alkoxy group by a known method, such as regulation of a reaction condition.

[Crosslinking Agent Composition for Aqueous Resin]

The crosslinking agent composition for aqueous resin of the present invention is one containing the aforementioned metal alkoxide (X) or (Y) and at least one compound selected from a polycarbodiimide and a polyoxazoline (hereinafter referred to as "compound (Z)").

By jointly using the metal alkoxide (X) or (Y) together with the compound (Z), an action of the compound (Z) as a crosslinking agent relative to the aqueous resin can be improved.

The metal alkoxide (X) or (Y) is excellent in hydrolysis resistance, and even with respect to an aqueous resin having water solubility or water dispersibility, it also has a function to improve the crosslinking reactivity of the compound (Z) relative to the hydrophilic crosslinking group of the aqueous resin.

The metal alkoxide (X) or (Y) slightly exhibits the crosslinking reactivity relative to the aqueous resin even by the addition of only such a metal alkoxide; however, in this case, the sufficient crosslinking reactivity as in the case of its joint use with the compound (Z) is not obtained.

(Aqueous Resin)

The aforementioned aqueous resin is a resin having water solubility or water dispersibility. The aforementioned aqueous resin is one which may be crosslinked with a crosslinking agent.

Specifically, the aqueous resin as referred to in the present invention refers to at least one resin containing at least any one of an alcoholic hydroxy group and a carboxy group. That is, the aqueous resin has, as a crosslinking group, an alcoholic hydroxy group and/or a carboxy group, each of which is a hydrophilic group.

In particular, the aforementioned crosslinking agent composition for aqueous resin may exhibit an effect for improving the crosslinking reactivity relative to such a crosslinking group.

Examples of the aqueous resin include a polyester resin, an acrylic resin, a polyurethane resin, an epoxy resin, and a styrene-acrylic resin. These may be a single material or may be a mixture of two or more thereof.

From the viewpoint of thoroughly exhibiting the effects of the present invention, in the case where the aqueous resin contains only the alcoholic hydroxy group between the alcoholic hydroxy group and the carboxy group, a hydroxyl value of the solid component (resin component) is preferably 5 mgKOH/g or more, more preferably 5 to 150 mgKOH/g, and still more preferably 5 to 100 mgKOH/g.

From the same viewpoint as mentioned above, in the case where the aqueous resin contains only the carboxy group between the alcoholic hydroxy group and the carboxy group, an acid value of the solid component (resin component) is preferably 5 mgKOH/g or more, more preferably 5 to 150 mgKOH/g, and still more preferably 5 to 100 mgKOH/g.

In addition, from the same viewpoint as mentioned above, in the case where the aqueous resin contains both an alcoholic hydroxy group and a carboxy group, a total sum of a hydroxyl value and an acid value of the solid component (resin component) is preferably 5 mgKOH/g or more, more preferably 5 to 150 mgKOH/g, and still more preferably 5 to 100 mgKOH/g.

The hydroxyl value and the acid value can be measured by a method described in JIS K0070:1992.

(Compound (Z))

The compound (Z) is at least one compound selected from a polycarbodiimide and a polyoxazoline. This compound (Z) is one having a crosslinking action relative to the aqueous resin.

Although such a compound is generally used as a crosslinking agent having reactivity relative to the carboxy group, it is inferior in reactivity relative to the alcoholic hydroxy group. In the present invention, by jointly using the metal alkoxide (X) or (Y) together with the compound (Z), the crosslinking reactivity of the resin having an alcoholic hydroxy group relative to the foregoing hydroxy group can be improved, and the crosslinking reactivity relative to the carboxy group can also be improved.

From the viewpoint of sufficiently improving the crosslinking reactivity, the content of the metal alkoxide (X) or (Y) in the aforementioned crosslinking agent composition for aqueous resin is preferably 0.1 to 500 parts by mass, more preferably 1.0 to 200 parts by mass, and more preferably 2.5 to 50 parts by mass based on 100 parts by mass of the total content of the compound (Z).

The polycarbodiimide means a compound having two or more carbodiimide groups and can be obtained through a decarboxylation condensation reaction of a diisocyanate by adopting a known synthesis method.

The diisocyanate is not particularly limited and may be any of a linear or alicyclic aliphatic diisocyanate, an aromatic diisocyanate, and a heterocyclic diisocyanate, and these may be used alone or may be used in combination of two or more thereof.

Examples of the linear aliphatic diisocyanate include tetramethylene diisocyanate, hexamethylene diisocyanate, dodecamethylene diisocyanate, and 2,2,4-trimethylhexamethylene diisocyanate.

Examples of the alicyclic diisocyanate include 1,4-bis(isocyanatomethyl) cyclohexane, 2,2-bis(4-isocyanatocyclohexyl)propane, isophorone diisocyanate, and dicyclohexylmethane-4,4'-diisocyanate.

Examples of the aromatic diisocyanate include toluene-2,4-diisocyanate, diphenylmethane-2,2'-diisocyanate, diphenylmethane-2,4'-diisocyanate, diphenylmethane-4,4'-diisocyanate, and 2,4,6-triisopropylbenzene-1,3-diyl diisocyanate.

Examples of the aromatic ring-containing aliphatic diisocyanate include 1,3-bis(2-isocyanato-2-propyl)benzene (common name: tetramethylxylylene diisocyanate).

Of these, from the viewpoint of easiness of availability, and easiness of synthesis of the polycarbodiimide, and so on, dicyclohexylmethane-4,4'-diisocyanate and tetramethylxylylene diisocyanate are preferred, and in particular, dicyclohexylmethane-4,4'-diisocyanate is suitably used.

As for the polycarbodiimide having an isocyanate group at an end thereof, it is preferred that the terminal isocyanate group is blocked through a reaction with a known terminal-blocking agent having a functional group having reactivity relative to the isocyanate group. Examples of the functional group include a hydroxy group, a carboxy group, an amino group, and an isocyanate group. In addition, from the viewpoint of using as a crosslinking agent relative to the aqueous resin, the functional group is preferably a hydrophilic group. Examples thereof include a polyalkylene glycol monohydrocarbyl ether, and specifically, a polyalkylene glycol monoalkyl ether, such as polyethylene glycol monomethyl ether and polyethylene glycol monoethyl ether, is preferred.

A mass average molecular weight of the polyalkylene glycol monohydrocarbyl ether is preferably 180 to 2,100, more preferably 200 to 2,000, and still more preferably 250 to 1,000 from the viewpoint of hydrophilicity of the polycarbodiimide, affinity with the metal alkoxide (X) or (Y), and affinity with the aqueous resin, and so on.

The polyoxazoline means a compound having two or more oxazoline groups, and the following low-molecular compounds or oxazoline group-containing polymers bonding to the polymer main chain at the 2-position thereof are generally used. These may be used alone or may be used in combination of two or more thereof.

Examples of the low-molecular compound of the polyoxazoline include bis(2-oxazolines), such as 2,2'-bis(2-oxazoline), 2,2'-methylenebis(2-oxazoline), 2,2'-ethylenebis(2-oxazoline), 2,2'-trimethylenebis(2-oxazoline), 2,2'-tetramethylenebis(2-oxazoline), 2,2'-hexamethylenebis(2-oxazoline). 2,2'-octamethylenebis(2-oxazoline), 2,2'-ethylenebis(4,4'-dimethyl-2-oxazoline), 2,2'-p-phenylenebis(2-oxazoline), 2,2'-m-phenylenebis(4,4'-dimethyl-2-oxazoline), bis(2-oxazolinylcyclohexane)sulfide, and bis(2-oxazolinylnorbornane)sulfide.

Examples of the oxazoline group-containing polymer include a homopolymer of an unsaturated oxazoline, such as 2-vinyl-2-oxazoline and 2-isopropenyl-2-oxazoline, or a copolymer thereof with other copolymerizable unsaturated compound.

As the polyoxazoline, commercially available products, such as "EPOCROS" (registered trademark) (manufactured by Nippon Shokubai Co., Ltd.) that is an oxazoline group-containing polymer, can be used.

(Other Components)

If desired, the aforementioned crosslinking agent composition for aqueous resin may contain, in addition to the metal alkoxide (X) or (Y) and the compound (Z), other components, such as a solvent and various additives, e.g., a dispersant and an antioxidant, according to the use purpose, the application, and so on. However, from the viewpoint of allowing the foregoing crosslinking agent composition to sufficiently exhibit the crosslinking reactivity, the total content of the metal alkoxide (X) or (Y) and the compound (Z) in the components other than the solvent in the crosslinking agent composition for aqueous resin is preferably 60% by mass or more, more preferably 80% by mass or more, and still more preferably 90% by mass or more.

From the viewpoint of uniformly mixing the respective components in the crosslinking agent composition for aqueous resin, the solvent is used as the need arises. The content thereof is not particularly limited and can be appropriately adjusted according to the handling properties at the time of use, and so on. The kind of the solvent is appropriately selected according to the kind and the use application of the resin, and so on, and the solvent is used upon being added to the aqueous resin. Thus, examples thereof include water and hydrophilic solvents, such as an alcohol, an ether, a ketone, and an ester. These may be used alone or may be used in combination of two or more thereof. Of these, water or a mixed solvent of water and a hydrophilic solvent is preferred, and from the viewpoint of environment and costs, and so on, the solvent is preferably water only. Such a solvent is occasionally contained in a product of the commercially available polycarbodiimide or polyoxazoline.

The content of the additive can be appropriately adjusted according to desired physical properties of an aqueous resin cured product to be produced within a range where the crosslinking reaction of the aqueous resin is not influenced.

[Aqueous Resin Composition]

The aqueous resin composition of the present invention is one containing the aforementioned aqueous resin, the compound (Z), and the metal alkoxide (X) or (Y). That is, this aqueous resin composition is one containing the aforementioned aqueous resin and the aforementioned crosslinking agent composition for aqueous resin.

The content of the compound (Z) in the aqueous resin composition is preferably 0.01 to 10 mol, more preferably 0.1 to 5.0 mol, and still more preferably 0.2 to 2.4 mol in terms of a sum total of the carbodiimide group of the polycarbodiimide and the oxazoline group of the polyoxazoline based on 1 mol of a sum total of the alcoholic hydroxy group and the carboxy group of the aforementioned aqueous resin.

The content of the metal alkoxide (X) or (Y) in the aqueous resin composition is preferably 0.005 to 5.0 parts by mass, more preferably 0.01 to 3.0 parts by mass, and still more preferably 0.03 to 2.0 parts by mass in total as expressed in terms of a metal element amount based on 100 parts by mass of a total sum of the aqueous resins.

If desired, the aforementioned aqueous resin composition may contain, in addition to the aqueous resin, the compound (Z), and the metal alkoxide (X) or (Y), other components, such as a solvent and various additives, e.g., a coloring agent, a filler, a dispersant, a plasticizer, a thickening agent, an ultraviolet absorber, and an antioxidant, according to the use purpose, the application, and so on. However, from the viewpoint of allowing the aqueous resin composition to produce a favorable aqueous resin cured product, the total content of the aqueous resin, the compound (Z), and the metal alkoxide (X) or (Y) in the components other than the solvent in the aqueous resin composition is preferably 60% by mass or more, more preferably 80% by mass or more, and still more preferably 90% by mass or more.

From the viewpoint of uniformly mixing the respective components in the aqueous resin composition, the solvent is one to be used as the need arises. The content thereof is not particularly limited and can be appropriately adjusted according to the handling properties at the time of use, and so on. The kind of the solvent is appropriately selected according to the kind and the use application of the resin, and so on, and the solvent is used upon being added to the aqueous resin. Thus, the solvent is preferably the aforementioned hydrophilic solvents. Such a solvent is occasionally contained in a product of the commercially available aqueous resin or compound (Z).

The content of the additive can be appropriately adjusted according to desired physical properties of a cured product of the aqueous resin composition within a range where the crosslinking reaction of the aqueous resin is not influenced. The total content of the additives is preferably 30 parts by mass or less, more preferably 25 parts by mass or less, and still more preferably 20 parts by mass or less based on 100 parts by mass of the aqueous resin.

The aqueous resin composition can be obtained by mixing and stirring the aqueous resin, the compound (Z), and the metal alkoxide (X) or (Y). A known method is applicable for mixing and stirring. The aforementioned additive or the like may be further added as an arbitrary component. The addition and mixing order of the respective components is not particularly limited. On the occasion of mixing and stirring, as mentioned above, from the viewpoint of uniformly mixing the respective blending components, a solvent may be appropriately used.

The aqueous resin composition is cured upon being heated, whereby an aqueous resin cured product having a high crosslinking degree is obtained. For this reason, the aqueous resin composition may exhibit excellent various physical properties due to the fact that it is an aqueous resin cured product having a high crosslinking degree in various applications, such as a paint, an ink, a fiber processing agent, an additive, a coating agent, and a molded product.

For example, when used as a paint, a cured coating film having a high crosslinking degree can be obtained, and this cured coating film has excellent water resistance and solvent resistance.

EXAMPLES

The present invention is hereunder described in detail by reference to Examples, but it should be construed that the present invention is not limited by these Examples.

Details of blending raw materials in production of each of aqueous resin compositions of the following Examples, Comparative Examples, and Synthesis Examples are as follows. In the following aqueous resins, it was considered that the hydroxyl value is a value based on an alcoholic hydroxy group, and the acid value is a value based on a carboxy group.

<Aqueous Resin>

Acrylic resin A (emulsion): "NeoCryl (registered trademark) XK-103", manufactured by DSM Coating Resins B.V., solid component (resin component): 45% by mass, dispersion medium: water, hydroxyl value (expressed in terms of a solid component): 47.2 mgKOH/g, acid value (expressed in terms of a solid component): 3.2 mgKOH/g Acrylic resin B (emulsion): "BURNOCK (registered trademark) WE-304", manufactured by DIC Corporation, solid component (resin component): 45% by mass, dispersion medium: water, hydroxyl value (expressed in terms of a solid component): 43 mgKOH/g Polyurethane resin dispersion: "SANCURE (registered trademark) 777", manufactured by The Lubrizol Corporation, solid component (resin component): 35% by mass, acid value (dispersion): 21.4 mgKOH/g, aqueous dispersion <Compound (Z)>

Polycarbodiimide (Z1): One produced by the following Synthesis Example P, solid component (component concentration): 40% by mass, polymerization degree: 6.5, solvent: water Polyoxazoline (Z2): "EPOCROS (registered trademark) WS500", manufactured by Nippon Shokubai Co., Ltd., oxazoline group-containing polymer, polymer main chain: acrylic, solid component (component concentration): 39% by mass, oxazoline equivalent: 220 (calculated value as expressed in terms of a solid component), solvent: water and 1-methoxy-2-propanol <Metal Alkoxide>

Titanium alkoxide (X1): One produced in the following Synthesis Example 1

Titanium alkoxide (Y1-1): One produced in the following Synthesis Example 2

Titanium alkoxide (Y1-2): One produced in the following Synthesis Example 3

Titanium alkoxide (Y1-3): One produced in the following Synthesis Example 4
Zirconium alkoxide (X2): One produced in the following Synthesis Example 5
Zirconium alkoxide (Y2-1): One produced in the following Synthesis Example 6
Zirconium alkoxide (Y2-2): One produced in the following Synthesis Example 7
Zirconium alkoxide (Y2-3): One produced in the following Synthesis Example 8
Aluminum alkoxide (X3): One produced in the following Synthesis Example 9
Aluminum alkoxide (Y3-1): One produced in the following Synthesis Example 10
Aluminum alkoxide (Y3-2): One produced in the following Synthesis Example 11
Titanium tetra-n-butoxide: "ORGATIX TA-21", manufactured by Matsumoto Fine Chemical Co., Ltd., molecular weight: 340.32

(Synthesis Example P) Synthesis of Polycarbodiimide 1,572 g of dicyclohexylmethane 4,4'-diisocyanate and 7.86 g of 3-methyl-1-phenyl-2-phospholene-1-oxide as a carbodiimidization catalyst were charged in a 3,000-mL reaction vessel equipped with a reflux tube and a stirrer and stirred under a nitrogen gas stream at 185° C. for 10 hours, to obtain an isocyanate-terminated polycarbodiimide that is a polymer of the dicyclohexylmethane 4,4'-diisocyanate.

This isocyanate-terminated polycarbodiimide was mixed with a toluene solution of di-n-butylamine having an already-known concentration, thereby allowing the terminal isocyanate group and the di-n-butylamine to react with each other. The residual di-n-butylamine was subjected to neutral titration with a hydrochloric acid standard solution, and the residual amount [% by mass] of the isocyanate group (terminal isocyanate group amount) was calculated by the potentiometric titration method (used device: automated titration device "COM-900", manufactured by Hiranuma Sangyo Co., Ltd.) and found to be 5.00% by mass. That is, a polymerization degree of this isocyanate-terminated polycarbodiimide (average content number of the carbodiimide group in one molecule) was 6.5.

51.8 g of the obtained isocyanate-terminated polycarbodiimide was dissolved at 120° C., to which was then added 24.7 g of polyethylene glycol monomethyl ether ("BLAUNON MP-400", manufactured by Aoki Oil Industrial Co., Ltd., molecular weight: 400 (catalogue value), hereinafter the same), and the contents were heated to 140° C. and allowed to react with each other for 5 hours while stirring. With respect to the reaction product, it was confirmed through infrared absorption spectrum measurement that the absorption of the isocyanate group at a wavelength of 2,200 to 2,300 cm$^{-1}$ vanished. Thereafter, the resultant was cooled to 80° C., to which was added 115 g of ion-exchanged water, followed by stirring for 1 hour, to obtain a polycarbodiimide aqueous solution having a solid component of 40% by mass.

(Synthesis Example 1) Synthesis of Titanium Alkoxide (X1)

50 g of titanium tetraisopropoxide ("TA-8", manufactured by Matsumoto Fine Chemical Co., Ltd., titanium content: 16.9% by mass) and 282 g of polyethylene glycol monomethyl ether ("BLAUNON MP-400") were charged in a reaction vessel equipped with a stirrer and stirred under a nitrogen gas stream at 90° C. for 24 hours, and isopropyl alcohol was discharged out the reaction vessel, to obtain a reaction product.

After 2.00 g of the obtained reaction product was weighed in an alumina-made crucible and heated at 600° C. for 3 hours, the amount of the residue (titanium oxide) was found to be 0.0969 g (titanium content in the reaction product: 2.91% by mass). In view of the fact that this titanium content was coincident with the titanium content in the alkoxide (mass average molecular weight: 1,644) in which four polyethylene glycol monomethyl ethers (molecular weight: 400) were bonded to one titanium atom, it was confirmed that the targeted titanium alkoxide (X1) was obtained.

(Synthesis Example 2) Synthesis of Titanium Alkoxide (Y1-1)

A reaction product was obtained in the same manner as in Synthesis Example 1, except that in Synthesis Example 1, the addition amount of the polyethylene glycol monomethyl ether was changed to 212 g.

After 2.00 g of the obtained reaction product was weighed in an alumina-made crucible and heated at 600° C. for 3 hours, the amount of the residue (titanium oxide) was found to be 0.122 g (titanium content in the reaction product: 3.66% by mass). From this fact, it was confirmed that the targeted titanium alkoxide (Y1-1) (mass average molecular weight: 1,304) in which three in average of four isopropoxy groups in one molecule of the titanium tetraisopropoxide were substituted with polyethylene glycol monomethyl ether (molecular weight: 400) was obtained.

(Synthesis Example 3) Synthesis of Titanium Alkoxide (Y1-2)

A reaction product was obtained in the same manner as in Synthesis Example 1, except that in Synthesis Example 1, the addition amount of the polyethylene glycol monomethyl ether was changed to 141 g.

After 2.00 g of the obtained reaction product was weighed in an alumina-made crucible and heated at 600° C. for 3 hours, the amount of the residue (titanium oxide) was found to be 0.165 g (titanium content in the reaction product: 4.95% by mass). From this fact, it was confirmed that the targeted titanium alkoxide (Y1-2) (mass average molecular weight: 968) in which two in average of four isopropoxy groups in one molecule of the titanium tetraisopropoxide were substituted with polyethylene glycol monomethyl ether (molecular weight: 400) was obtained.

(Synthesis Example 4) Synthesis of Titanium Alkoxide (Y1-3)

A reaction product was obtained in the same manner as in Synthesis Example 1, except that in Synthesis Example 1, the addition amount of the polyethylene glycol monomethyl ether was changed to 71 g.

After 2.00 g of the obtained reaction product was weighed in an alumina-made crucible and heated at 600° C. for 3 hours, the amount of the residue (titanium oxide) was found to be 0.254 g (titanium content in the reaction product: 7.63% by mass). From this fact, it was confirmed that the targeted titanium alkoxide (Y1-3) (mass average molecular weight: 628) in which one in average of four isopropoxy groups in one molecule of the titanium tetraisopropoxide was substituted with polyethylene glycol monomethyl ether (molecular weight: 400) was obtained.

(Synthesis Example 5) Synthesis of Zirconium Alkoxide (X2)

50 g of zirconium tetra-n-propoxide ("ZA-45", manufactured by Matsumoto Fine Chemical Co., Ltd., zirconium content: 21.0% by mass) and 184 g of polyethylene glycol monomethyl ether ("BLAUNON MP-400") were charged in a reaction vessel equipped with a stirrer and stirred under a nitrogen gas stream at 90° C. for 24 hours, and n-propyl alcohol was discharged out the reaction vessel, to obtain a reaction product.

After 2.00 g of the obtained reaction product was weighed in an alumina-made crucible and heated at 600° C. for 3 hours, the amount of the residue (zirconium oxide) was found to be 0.146 g (zirconium content in the reaction product: 5.40% by mass). In view of the fact that this zirconium content was coincident with the zirconium content in the alkoxide (mass average molecular weight: 1,687) in which four polyethylene glycol monomethyl ethers (molecular weight: 400) were bonded to one zirconium atom, it was confirmed that the targeted zirconium alkoxide (X2) was obtained.

(Synthesis Example 6) Synthesis of Zirconium Alkoxide (Y2-1)

A reaction product was obtained in the same manner as in Synthesis Example 5, except that in Synthesis Example 5, the addition amount of the polyethylene glycol monomethyl ether was changed to 138 g.

After 2.00 g of the obtained reaction product was weighed in an alumina-made crucible and heated at 600° C. for 3 hours, the amount of the residue (zirconium oxide) was found to be 0.182 g (zirconium content in the reaction product: 6.74% by mass). From this fact, it was confirmed that the targeted zirconium alkoxide (Y2-1) (mass average molecular weight: 1,347) in which three in average of four isopropoxy groups in one molecule of the zirconium tetraisopropoxide were substituted with polyethylene glycol monomethyl ether (molecular weight: 400) was obtained.

(Synthesis Example 7) Synthesis of Zirconium Alkoxide (Y2-2)

A reaction product was obtained in the same manner as in Synthesis Example 5, except that in Synthesis Example 5, the addition amount of the polyethylene glycol monomethyl ether was changed to 92 g.

After 2.00 g of the obtained reaction product was weighed in an alumina-made crucible and heated at 600° C. for 3 hours, the amount of the residue (zirconium oxide) was found to be 0.244 g (zirconium content in the reaction product: 9.02% by mass). From this fact, it was confirmed that the targeted zirconium alkoxide (Y2-2) (mass average molecular weight: 1,011) in which two in average of four isopropoxy groups in one molecule of the zirconium tetraisopropoxide were substituted with polyethylene glycol monomethyl ether (molecular weight: 400) was obtained.

(Synthesis Example 8) Synthesis of Zirconium Alkoxide (Y2-3)

A reaction product was obtained in the same manner as in Synthesis Example 5, except that in Synthesis Example 5, the addition amount of the polyethylene glycol monomethyl ether was changed to 46 g.

After 2.00 g of the obtained reaction product was weighed in an alumina-made crucible and heated at 600° C. for 3 hours, the amount of the residue (zirconium oxide) was found to be 0.367 g (zirconium content in the reaction product: 6.74% by mass). From this fact, it was confirmed that the targeted zirconium alkoxide (Y2-3) (mass average molecular weight: 671) in which one in average of four isopropoxy groups in one molecule of the zirconium tetraisopropoxide was substituted with polyethylene glycol monomethyl ether (molecular weight: 400) was obtained.

(Synthesis Example 9) Synthesis of Aluminum Alkoxide (X3)

50 g of aluminum trisecondary butoxide ("AL-3001", manufactured by Matsumoto Fine Chemical Co., Ltd., aluminum content: 10.7% by mass) and 238 g of polyethylene glycol monomethyl ether ("BLAUNON MP-400") were charged in a reaction vessel equipped with a stirrer and stirred under a nitrogen gas stream at 90° C. for 24 hours, and isopropyl alcohol was discharged out the reaction vessel, to obtain a reaction product.

After 2.00 g of the obtained reaction product was weighed in an alumina-made crucible and heated at 600° C. for 3 hours, the amount of the residue (aluminum oxide) was found to be 0.0831 g (aluminum content in the reaction product: 2.20% by mass). In view of the fact that this aluminum content was coincident with the aluminum content in the alkoxide (mass average molecular weight: 1,224) in which three polyethylene glycol monomethyl ethers (molecular weight: 400) were coordinated with one aluminum atom, it was confirmed that the targeted aluminum alkoxide (X3) was obtained.

(Synthesis Example 10) Synthesis of Aluminum Alkoxide (Y3-1)

A reaction product was obtained in the same manner as in Synthesis Example 9, except that in Synthesis Example 9, the addition amount of the polyethylene glycol monomethyl ether was changed to 159 g.

After 2.00 g of the obtained reaction product was weighed in an alumina-made crucible and heated at 600° C. for 3 hours, the amount of the residue (aluminum oxide) was found to be 0.113 g (aluminum content in the reaction product: 3.00% by mass). From this fact, it was confirmed that the targeted aluminum alkoxide (Y3-1) (mass average molecular weight: 898) in which two in average of three secondary butoxy groups in one molecule of the aluminum trisecondary butoxide were substituted with polyethylene glycol monomethyl ether (molecular weight: 400) was obtained.

(Synthesis Example 11) Synthesis of Aluminum Alkoxide (Y3-2)

A reaction product was obtained in the same manner as in Synthesis Example 9, except that in Synthesis Example 9, the addition amount of the polyethylene glycol monomethyl ether was changed to 79 g.

After 2.00 g of the obtained reaction product was weighed in an alumina-made crucible and heated at 600° C. for 3 hours, the amount of the residue (aluminum oxide) was found to be 0.178 g (aluminum content in the reaction product: 4.71% by mass). From this fact, it was confirmed that the targeted aluminum alkoxide (Y3-2) (mass average molecular weight: 573) in which one in average of three secondary butoxy groups in one molecule of the aluminum trisecondary butoxide was substituted with polyethylene glycol monomethyl ether (molecular weight: 400) was obtained.

[Production of Aqueous Acrylic Resin Composition]

Example 1

In a 200-mL plastic container, 100 g of the acrylic resin A (emulsion) as an aqueous resin, 18 g of the polycarbodiimide (Z1) (carbodiimide group: 0.5 mol per mol of the alcoholic hydroxy group of the aqueous resin), and 2.0 g of the titanium alkoxide (X1) (0.13 parts by mass based on 100 parts by mass of the aqueous resin (solid component) as expressed in terms of a metal element amount) were weighed and mixed and stirred for 1 hour, to obtain an aqueous acrylic resin composition.

Examples 2 to 19

Each of aqueous acrylic resin compositions was obtained in the same manner as in Example 1, except for using a blending composition as shown in the following Table 1.

Comparative Examples 1 to 9

Each of aqueous acrylic resin compositions was obtained in the same manner as in Example 1, except for using a blending composition as shown in the following Table 2.

[Solvent Resistance Evaluation (1) of Coating Film]

Using each of the aqueous acrylic resin compositions obtained the aforementioned Examples and Comparative Examples, a coating film sample was prepared in the following manner, and a solvent resistance test of the coating film sample was performed. For reference, a coating film sample prepared using only the acrylic resin A was designated as Comparative Example 10, and this was subjected to the same test.

(Preparation of Coating Film Sample)

The aqueous acrylic resin composition immediately after preparation through stirring with a stirrer in a beaker for 1 hour was coated in a thickness of about 60 μm on an aluminum plate substrate by using a bar coater and dried for 10 minutes in a drying machine at a setting temperature of 130° C. Thereafter, the resultant was aged in a room at 25° C. for 1 day, to obtain a coating film sample.

In addition, the above-prepared aqueous acrylic resin composition was stored in a room at 25° C. for 1 week, and using this aqueous acrylic resin composition, a coating film sample was prepared in the same manner.

(Solvent Resistance Test)

Each of the above-prepared coating film samples was subjected to a solvent resistance test by performing reciprocal double rubbing of 50 times with cotton wool impregnated with a 95% by volume ethanol aqueous solution as a solvent (load: 900 g/cm$^2$) using a friction tester ("Model FR-1B", manufactured by Suga Test Instruments Co., Ltd.). The solvent resistance of the coating film is an index of the crosslinking degree of a cured coating film of the aqueous resin composition, and it is expressed that the higher the crosslinking degree, the more excellent the solvent resistance is.

The state of the coating film sample after the test was visually observed and evaluated according to the following evaluation criteria.

<Evaluation Criteria>

A: The coating film was not changed (colorless and transparent) or had thin rubbing marks.

B: The coating film was partially whitened.

C: The coating film was entirely whitened.

D: A part of the coating film was dissolved, and a part of the substrate at the rubbed place was exposed.

E: The coating film was dissolved, and the whole of the substrate at the rubbed place was exposed.

The coating film graded as "Evaluation A" has sufficient solvent resistance, and it may be said that the cured coating film of the aqueous resin composition has a sufficiently high crosslinking degree. The coating film graded as "Evaluation B" is inferior to one graded as "Evaluation A", but it may be said that the cured coating film has solvent resistance and has a high crosslinking degree. The coating films graded as "Evaluation C" and "Evaluation D" are not said to be sufficient in terms of the solvent resistance and are insufficient in terms of the crosslinking degree; and it may be considered that the coating film graded as "Evaluation C" is low in terms of the crosslinking degree, and the coating film graded as "Evaluation D" is very low in terms of the crosslinking degree or is not substantially crosslinked. The coating film graded as "Evaluation E" can be considered to be not crosslinked. These evaluation results are shown in the following Tables 1 and 2.

TABLE 1

| Blending composition [g] | Example | | | | | | | | | |
|---|---|---|---|---|---|---|---|---|---|---|
| | 1 | 2 | 3 | 4 | 5 | 6 | 7 | 8 | 9 | 10 |
| Aqueous resin | | | | | | | | | | |
| Acrylic resin A (emulsion) (solid component: 45% by mass) | 100 | 100 | 100 | 100 | 100 | 100 | 100 | 100 | 100 | 100 |
| Acrylic resin B (emulsion) (solid component: 45% by mass) | | | | | | | | | | |
| Compound (Z) | | | | | | | | | | |
| Polycarbodiimide (Z1) (solid component: 40% by mass) | 18 | 18 | 18 | 18 | 18 | 18 | 18 | 18 | 18 | 18 |
| Polyoxazoline (Z2) (solid component: 39% by mass) | | | | | | | | | | |

TABLE 1-continued

| | 1 | 2 | 3 | 4 | 5 | 6 | 7 | 8 | 9 | 10 |
|---|---|---|---|---|---|---|---|---|---|---|
| (Carbodiimide group or oxazoline group [mol] (vs. alcoholic hydroxy group or carboxy group of aqueous resin: total: 1 mol)) | (0.5) | (0.5) | (0.5) | (0.5) | (0.5) | (0.5) | (0.5) | (0.5) | (0.5) | (0.5) |
| Metal alkoxide | | | | | | | | | | |
| Titanium alkoxide (X1) | 2.0 | 0.33 | 0.67 | 17.3 | 34.5 | | | | | |
| Titanium alkoxide (Y1-1) | | | | | | 1.6 | | | | |
| Titanium alkoxide (Y1-2) | | | | | | | 1.2 | | | |
| Zirconium alkoxide (X2) | | | | | | | | 1.1 | | |
| Zirconium alkoxide (Y2-1) | | | | | | | | | 0.89 | |
| Zirconium alkoxide (Y2-2) | | | | | | | | | | 0.7 |
| Aluminum alkoxide (X3) | | | | | | | | | | |
| Aluminum alkoxide (Y3-1) | | | | | | | | | | |
| (Expressed in terms of a metal element amount [parts by mass] (vs. 100 parts by mass of aqueous resin)) | (0.13) | (0.02) | (0.04) | (2.1) | (2.2) | (0.13) | (0.13) | (0.13) | (0.13) | (0.13) |
| Solvent resistance evaluation of coating film | | | | | | | | | | |
| Immediately after preparation | B | B | B | B | B | B | B | B | B | B |
| Stored for 1 week | A | B | A | B | B | A | A | A | A | A |

| | Example | | | | | | | | |
|---|---|---|---|---|---|---|---|---|---|
| Blending composition [g] | 11 | 12 | 13 | 14 | 15 | 16 | 17 | 18 | 19 |
| Aqueous resin | | | | | | | | | |
| Acrylic resin A (emulsion) (solid component: 45% by mass) | 100 | 100 | 100 | 100 | 100 | 100 | | 100 | 100 |
| Acrylic resin B (emulsion) (solid component: 45% by mass) | | | | | | | 100 | | |
| Compound (Z) | | | | | | | | | |
| Polycarbodiimide (Z1) (solid component: 40% by mass) | 18 | 18 | 3.6 | 7.2 | 72 | 90 | 18 | | |
| Polyoxazoline (Z2) (solid component: 39% by mass) | | | | | | | | 10 | 10 |
| (Carbodiimide group or oxazoline group [mol] (vs. alcoholic hydroxy group or carboxy group of aqueous resin: total: 1 mol)) | (0.5) | (0.5) | (0.1) | (0.2) | (0.2) | (2.5) | (0.5) | (0.5) | (0.5) |
| Metal alkoxide | | | | | | | | | |
| Titanium alkoxide (X1) | | | 2.0 | 2.0 | 2.0 | 2.0 | 2.0 | 2.0 | |
| Titanium alkoxide (Y1-1) | | | | | | | | | 1.6 |
| Titanium alkoxide (Y1-2) | | | | | | | | | |
| Zirconium alkoxide (X2) | | | | | | | | | |
| Zirconium alkoxide (Y2-1) | | | | | | | | | |
| Zirconium alkoxide (Y2-2) | | | | | | | | | |
| Aluminum alkoxide (X3) | 2.7 | | | | | | | | |
| Aluminum alkoxide (Y3-1) | | 2.9 | | | | | | | |
| (Expressed in terms of a metal element amount [parts by mass] (vs. 100 parts by mass of aqueous resin)) | (0.13) | (0.13) | (0.13) | (0.13) | (0.13) | (0.13) | (0.13) | (0.13) | (0.13) |
| Solvent resistance evaluation of coating film | | | | | | | | | |
| Immediately after preparation | B | B | B | B | B | B | B | A | A |
| Stored for 1 week | A | A | B | A | A | B | A | A | A |

TABLE 2

| Blending composition [g] | Comparative Example | | | | | | | | | |
|---|---|---|---|---|---|---|---|---|---|---|
| | 1 | 2 | 3 | 4 | 5 | 6 | 7 | 8 | 9 | 10 |
| Aqueous resin | | | | | | | | | | |
| Acrylic resin A (emulsion) (solid component: 45% by mass) | 100 | 100 | 100 | 100 | 100 | | 100 | 100 | 100 | 100 |
| Acrylic resin B (emulsion) (solid component: 45% by mass) | | | | | | 100 | | | | |
| Compound (Z) | | | | | | | | | | |
| Polycarbodiimide (Z1) (solid component: 40% by mass) | 18 | 18 | 18 | 18 | 18 | 18 | | | | |
| Polyoxazoline (Z2) (solid component: 39% by mass) | | | | | | | | 10 | | |
| (Carbodiimide group or oxazoline group [mol] (vs. alcoholic hydroxy group or carboxy group of aqueous resin: total: 1 mol)) | (0.5) | (0.5) | (0.5) | (0.5) | (0.5) | (0.5) | (0.5) | | | |
| Metal alkoxide | | | | | | | | | | |
| Titanium alkoxide (X1) | | | | | | | | 2.0 | | |
| Titanium alkoxide (Y1-1) | | | | | | | | | 1.6 | |
| Titanium alkoxide (Y1-3) | 0.77 | | | | | | | | | |
| Zirconium alkoxide (Y2-3) | | 0.4 | | | | | | | | |
| Aluminum alkoxide (Y3-2) | | | 1.24 | | | | | | | |
| Titanium tetra-n-butoxide | | | | 0.43 | | | | | | |
| (Expressed in terms of a metal element amount [parts by mass] (vs. 100 parts by mass of aqueous resin)) | (0.13) | (0.13) | (0.13) | (0.13) | | | | (0.13) | (0.13) | |
| Solvent resistance evaluation of coating film | | | | | | | | | | |
| Immediately after preparation | C | C | C | C | C | E | C | D | D | E |
| Stored for 1 week | C | C | C | C | C | E | C | D | D | E |

[Production of Aqueous Polyurethane Resin Composition]

Example 20

In a 200-mL plastic container, 100 g of the polyurethane resin dispersion as an aqueous resin, 7.00 g of the polycarbodiimide compound (Z1) (carbodiimide group: 0.66 mol per mol of the carboxy group of the aqueous resin), and 2.0 g of the titanium alkoxide compound (X1) (0.17 parts by mass based in 100 parts by mass of the aqueous resin (solid component) as expressed in terms of a metal element amount) were weighed and mixed and stirred for 1 hour, to obtain an aqueous polyurethane resin composition.

Examples 21 to 27 and Comparative Examples 11 to 14

Each of aqueous polyurethane resin compositions was obtained in the same manner as in Example 20, except for using a blending composition as shown in the following Table 3.

[Solvent Resistance Evaluation (2) of Coating Film]

Using each of the aqueous polyurethane resin compositions obtained the aforementioned Examples and Comparative Examples, a coating film sample was prepared in the following manner, and a solvent resistance test of the coating film sample was performed.

(Preparation of Coating Film Sample)

The aqueous polyurethane resin composition immediately after preparation through stirring with a stirrer in a beaker for 1 hour was coated in a thickness of about 60 μm on an aluminum plate substrate by using a bar coater and dried for 5 hours in a room at a setting temperature of 25° C., to obtain a coating film sample.

(Solvent Resistance Test)

Each of the above-prepared coating film samples was subjected to a solvent resistance test by performing reciprocal double rubbing of 100 times with cotton wool impregnated with a 95% by volume ethanol aqueous solution as a solvent (load: 900 g/cm$^2$) using a friction tester ("Model FR-1B", manufactured by Suga Test Instruments Co., Ltd.). The solvent resistance of the coating film is an index of the crosslinking degree of a cured coating film of the aqueous resin composition, and it is expressed that the higher the crosslinking degree, the more excellent the solvent resistance is.

The state of the coating film sample after the test was visually observed and evaluated according to the following evaluation criteria.

<Evaluation Criteria>
A: The coating film was not changed.
B: The coating film was whitened and scratched.
C: The coating film was pierced, and a part of the substrate at the rubbed place was exposed.
D: The coating film was dissolved, and the whole of the substrate at the rubbed place was exposed.

The coating film graded as "Evaluation A" has sufficient solvent resistance, and it may be said that the cured coating film of the aqueous resin composition has a sufficiently high crosslinking degree. The coating film graded as "Evaluation B" is inferior to one graded as "Evaluation A", but it may be said that the cured coating film has solvent resistance and has a high crosslinking degree. The coating films graded as "Evaluation C" and "Evaluation D" are not said to be sufficient in terms of the solvent resistance and are insufficient in terms of the crosslinking degree; and it may be considered that the coating film graded as "Evaluation C" is low in terms of the crosslinking degree, and the coating film graded as "Evaluation D" is very low in terms of the crosslinking degree or is not substantially crosslinked.

These evaluation results are shown in the following Table 3.

TABLE 3

| Blending composition [g] | Example 20 | 21 | 22 | 23 | 24 | 25 | 26 |
|---|---|---|---|---|---|---|---|
| Aqueous resin | | | | | | | |
| Polyurethane resin dispersion (solid component: 35% by mass) | 100 | 100 | 100 | 100 | 100 | 100 | 100 |
| Compound (Z) | | | | | | | |
| Polycarbodiimide (Z1) (solid component: 40% by mass) | 7.0 | 7.0 | 7.0 | 7.0 | 7.0 | 7.0 | 7.0 |
| (Carbodiimide group [mol] (vs. carboxy group of aqueous resin: total: 1 mol)) | (0.66) | (0.66) | (0.66) | (0.66) | (0.66) | (0.66) | (0.66) |
| Metal alkoxide | | | | | | | |
| Titanium alkoxide (X1) | 2.0 | | | | | | |
| Titanium alkoxide (Y1-1) | | 1.6 | | | | | |
| Titanium alkoxide (Y1-2) | | | 1.2 | | | | |
| Zirconium alkoxide (X2) | | | | 1.1 | | | |
| Zirconium alkoxide (Y2-1) | | | | | 0.89 | | |
| Zirconium alkoxide (Y2-2) | | | | | | 0.7 | |
| Aluminum alkoxide (X3) | | | | | | | 2.7 |
| Aluminum alkoxide (Y3-1) | | | | | | | |
| (Expressed in terms of a metal element amount [parts by mass] (vs. 100 parts by mass of aqueous resin)) | (0.17) | (0.17) | (0.17) | (0.17) | (0.17) | (0.17) | (0.17) |
| Solvent resistance evaluation of coating film | A | A | A | A | A | A | A |

| Blending composition [g] | Example 27 | Comparative Example 11 | 12 | 13 | 14 |
|---|---|---|---|---|---|
| Aqueous resin | | | | | |
| Polyurethane resin dispersion (solid component: 35% by mass) | 100 | 100 | 100 | 100 | 100 |
| Compound (Z) | | | | | |
| Polycarbodiimide (Z1) (solid component: 40% by mass) | 7.0 | | | | 7.0 |
| (Carbodiimide group [mol] (vs. carboxy group of aqueous resin: total: 1 mol)) | (0.66) | | | | (0.66) |
| Metal alkoxide | | | | | |
| Titanium alkoxide (X1) | | 2.0 | | | |
| Titanium alkoxide (Y1-1) | | | | | |
| Titanium alkoxide (Y1-2) | | | | | |
| Zirconium alkoxide (X2) | | | 1.1 | | |
| Zirconium alkoxide (Y2-1) | | | | | |
| Zirconium alkoxide (Y2-2) | | | | | |
| Aluminum alkoxide (X3) | | | | 2.7 | |
| Aluminum alkoxide (Y3-1) | 2.9 | | | | |
| (Expressed in terms of a metal element amount [parts by mass] (vs. 100 parts by mass of aqueous resin)) | (0.17) | (0.17) | (0.17) | (0.17) | |
| Solvent resistance evaluation of coating film | A | D | D | D | C |

As noted from the evaluation results shown in Tables 1 to 3, it was perceived that the coating film formed using the aqueous resin composition of the present invention has a sufficiently high crosslinking degree. That is, it was perceived that by jointly using the compound (Z) and the metal alkoxide (X) or (Y), the crosslinking reactivity relative to the hydrophilic crosslinking group of the aqueous resin can be improved.

The invention claimed is:

1. A crosslinking agent composition for aqueous resin, comprising a metal alkoxide represented by the following formula (1-1), (1-2), or (1-3) and having a mass average molecular weight of 800 to 8,500:

$$Ti(OA)_4 \tag{1-1}$$

$$Zr(OA)_4 \tag{1-2}$$

$$Al(OA)_3 \tag{1-3}$$

wherein A's are each independently a residue resulting from removal of a hydroxy group from a polyalkylene glycol monohydrocarbyl ether represented by the following general formula (1a):

$$R^{11}(OCHR^{12}CH_2)_nOH \tag{1a}$$

wherein $R^{11}$ is an alkyl group having 1 to 4 carbon atoms or a phenyl group; $R^{12}$ is a hydrogen atom or an alkyl group having 1 to 4 carbon atoms; and n is an integer of 4 to 45,

OR a metal alkoxide represented by the following formula (2-1), (2-2), or (2-3) and having a mass average molecular weight of 600 to 6,000:

$$Ti(OA)_p(OR)_{4-p} \tag{2-1}$$

$$Zr(OA)_q(OR)_{4-q} \tag{2-2}$$

$$Al(OA)_r(OR)_{3-r} \tag{2-3}$$

wherein A's are each independently a residue resulting from removal of a hydroxy group from a polyalkylene glycol monohydrocarbyl ether represented by the following general formula (1a); R's are each independently an alkyl group having 1 to 20 carbon atoms; p and q are each a number of 2 or more and less than 4; and r is a number pf 2 or more and less than 3:

$$R^{11}(OCHR^{12}CH_2)_nOH \tag{1a}$$

wherein $R^{11}$ is an alkyl group having 1 to 4 carbon atoms or a phenyl group: $R^{12}$ is a hydrogen atom or an alkyl group having 1 to 4 carbon atoms; and n is an integer of 4 to 45; and at least one compound selected from a polycarbodiimide and a polyoxazoline.

2. An aqueous resin composition comprising at least one aqueous resin containing at least any one of an alcoholic hydroxy group and a carboxy group, at least one compound selected from a polycarbodiimide and a polyoxazoline, and a metal alkoxide represented by the following formula (1-1), (1-2), or (1-3) and having a mass average molecular weight of 800 to 8,500:

$$Ti(OA)_4 \tag{1-1}$$

$$Zr(OA)_4 \tag{1-2}$$

$$Al(OA)_3 \tag{1-3}$$

wherein A's are each independently a residue resulting from removal of a hydroxy group from a polyalkylene glycol monohydrocarbyl ether represented by the following general formula (1a):

$$R^{11}(OCHR^{12}CH_2)_nOH \tag{1a}$$

wherein $R^{11}$ is an alkyl group having 1 to 4 carbon atoms or a phenyl group; $R^{12}$ is a hydrogen atom or an alkyl group having 1 to 4 carbon atoms; and n is an integer of 4 to 45,

OR a metal alkoxide represented by the following formula (2-1), (2-2), or (2-3) and having a mass average molecular weight of 600 to 6,000:

$$Ti(OA)_p(OR)_{4-p} \tag{2-1}$$

$$Zr(OA)_q(OR)_{4-q} \tag{2-2}$$

$$Al(OA)_r(OR)_{3-r} \tag{2-3}$$

wherein A's are each independently a residue resulting from removal of a hydroxy group from a polyalkylene glycol monohydrocarbyl ether represented by the following general formula (1a); R's are each independently an alkyl group having 1 to 20 carbon atoms; p and a are each a number of 2 or more and less than 4; and r is a number of 2 or more and less than 3;

$$R^{11}(OCHR^{12}CH_2)_nOH \tag{1a}$$

wherein $R^{11}$ is an alkyl group having 1 to 4 carbon atoms or a phenyl group; $R^{12}$ is a hydrogen atom or an alkyl group having 1 to 4 carbon atoms; and n is an integer of 4 to 45.

* * * * *